United States Patent
Stefanile et al.

(10) Patent No.: US 6,312,453 B1
(45) Date of Patent: *Nov. 6, 2001

(54) DEVICE FOR COOLING INFANT'S BRAIN

(75) Inventors: Joseph P. Stefanile, Issaquah; Dale J. Dell'Ario, Shoreline; Steven G. Miles, Tacoma, all of WA (US)

(73) Assignee: Olympic Medical Corp., Seattle, WA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/116,827

(22) Filed: Jul. 16, 1998

(51) Int. Cl.[7] .................................................. A61F 7/00
(52) U.S. Cl. .................................... 607/109; 607/108
(58) Field of Search ............................. 607/104, 108, 607/109, 112

(56) References Cited

U.S. PATENT DOCUMENTS

| | | | |
|---|---|---|---|
| 1,627,523 | * 5/1927 | Morris | 607/109 |
| 4,026,299 | 5/1977 | Sauder. | |
| 4,149,541 | 4/1979 | Gammons et al.. | |
| 4,190,054 | 2/1980 | Brennan. | |
| 4,204,543 | 5/1980 | Henderson. | |
| 4,459,468 | 7/1984 | Bailey. | |
| 4,483,021 | 11/1984 | McCall. | |
| 4,552,149 | 11/1985 | Tatsuki. | |
| 4,566,455 | 1/1986 | Kramer. | |
| 4,641,655 | 2/1987 | Abt. | |
| 4,672,968 | 6/1987 | Lenox et al.. | |
| 4,750,493 | 6/1988 | Brader. | |
| 4,753,242 | 6/1988 | Saggers. | |
| 4,781,193 | 11/1988 | Pagden. | |
| 4,854,319 | 8/1989 | Tobin. | |
| 4,869,250 | 9/1989 | Bitterly. | |

(List continued on next page.)

FOREIGN PATENT DOCUMENTS

| | | |
|---|---|---|
| 0 158 470 | 10/1985 | (EP). |
| 0158470 | 10/1985 | (EP). |
| 9000752 | 10/1991 | (NL). |
| 446015 | * 11/1974 | (SU) .................. 607/109 |
| WO 82/04184 | 12/1982 | (WO). |
| WO 96/32855 | 10/1996 | (WO). |
| WO 98/16176 | 4/1998 | (WO). |

OTHER PUBLICATIONS

Clifton, Guy L. et al.; "A Phase II Study of Moderate Hypothermia in Severe Brain Injury"; *Journal of Neurotrauma*; 10(3):263–271; 1993.

Dietrich, W. Dalton et al.; "Intraischemic but Not Postischemic Brain Hypothermia Protects Chronically Following Global Forebrain Ischemia in Rats"; *Journal of Cerebral Blood Flow and Metabolism*; 13:541–549; 1993.

Gluckman, P.D. et al.; "The Effect of Cooling on Breathing and Shivering in Unanaesthetized Fetal Lambs in Utero"; *J. Physiol*; 343:495–506; 1983.

Green, E.J. et al.; "Combined postischemic hypothermia and delayed MK–801 treatment attenuates neurobehavioral deficits associated with transient global ischemia in rats"; *Brain Research*; 702:145–152; 1995.

(List continued on next page.)

Primary Examiner—Linda C. M. Dvorak
Assistant Examiner—R. Kearney
(74) Attorney, Agent, or Firm—Christensen O'Connor Johnson Kindness PLLC

(57) ABSTRACT

A device for cooling an infant's brain includes a cooling liner that may be sandwiched between an outer padded cap and an inner elastic liner. The device fits closely over the infant's skull and is cooled by a recirculating cooling fluid passing through a serpentine conduit. One application for the device is to cool a newborn infant's brain that has suffered a hypoxic shock.

9 Claims, 7 Drawing Sheets

U.S. PATENT DOCUMENTS

| | | |
|---|---|---|
| 4,920,963 | 5/1990 | Brader . |
| 4,987,896 | 1/1991 | Nakamatsu . |
| 5,174,285 | 12/1992 | Fontenot . |
| 5,197,292 | 3/1993 | McPherson . |
| 5,236,908 | 8/1993 | Gruber et al. . |
| 5,241,959 | 9/1993 | Kim et al. . |
| 5,261,399 | 11/1993 | Klatz et al. . |
| 5,269,369 | 12/1993 | Faghri . |
| 5,305,470 | 4/1994 | McKay . |
| 5,342,411 | 8/1994 | Maxted et al. . |
| 5,400,617 | 3/1995 | Ragonesi et al. . |
| 5,405,671 | 4/1995 | Kamin et al. . |
| 5,449,379 | 9/1995 | Hadtke . |
| 5,456,703 | 10/1995 | Beeuwkes, III . |
| 5,486,204 | 1/1996 | Clifton . |
| 5,500,007 | 3/1996 | Kim et al. . |
| 5,507,792 | 4/1996 | Mason et al. . |
| 5,514,170 | 5/1996 | Mauch . |
| 5,562,604 | 10/1996 | Yablon et al. . |
| 5,588,968 | 12/1996 | Sternlicht . |
| 5,603,728 | 2/1997 | Pachys . |
| 5,643,336 | 7/1997 | Lopez-Claros . |

OTHER PUBLICATIONS

Gunn, Alistair J. et al.; "Dramatic Neuronal Rescue with Prolonged Selective Head Cooling after Ischmeia in Fetal Lambs"; *The American Society for Clinical Investigation, Inc.*; 99(2);248–256; Jan. 1997.

Guy, Roland et al.; "Scalp Cooling by Thermocirculator"; *The Lancet*; pp. 937–938; Apr. 24, 1982.

Laptook. A.R. and Corbett, R.J.T.; "Therapeutic hypothermia: a potential neuroprotective and resuscitative strategy for neonatal hypoxiaischemia", *Prenat. Neonat Med.*, 1:199–212; 1996.

Leonov, Yuval et al.; "Mild Cerebral Hypothermia during and after Cardiac Arrest Improves Neurologic Outcome in Dogs"; *Journal of Cerebral Blood Flow and Metabolism*; 10:57–70; 1990.

Marion, Donald W. et al., "Resuscitative hypothermia"; *Crit. Care med.*, 24(2):S81–S89; 1996.

Safar, Peter et al.; "Improved Cerebral Resuscitationn From Cardiac Arrest in Dogs With Mild Hypothermia Plus Blood Flow Promotion"; *Stroke*; 27(1):105–113; Jan. 1996.

Sirimanne, E.S. et al; "The Effect of Prolonged Modification of Cerebral Temperature on Outcome after Hypoxic–Ischemic Brain Injury in the Infant Rat"; *Pediatric Research*; 39(4):591–597; 1996.

Sterz, Fritz et al.; "Mild hypothermic cardiopulmonary resuscitation improves outcome after prolonged cardiac arrest in dogs"; *Critical Care Medicine*; 19(3):379–389; Mar. 1991.

Moffat and Hackel; "The Effects of Hypothermia"; p. 172; 1985.

"Is a Neutral Temperature Optimal?"; *Thermoregulation in the Newborn* p. 208; 1987.

* cited by examiner

Fig. 1.
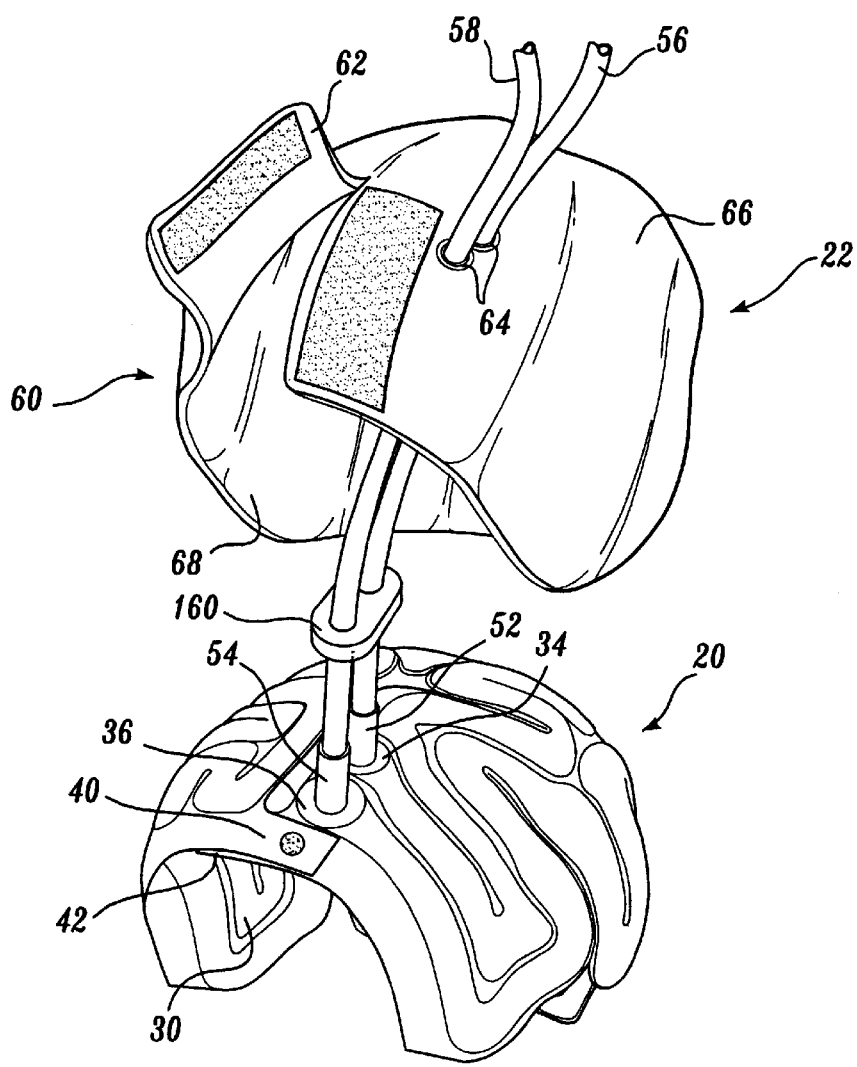
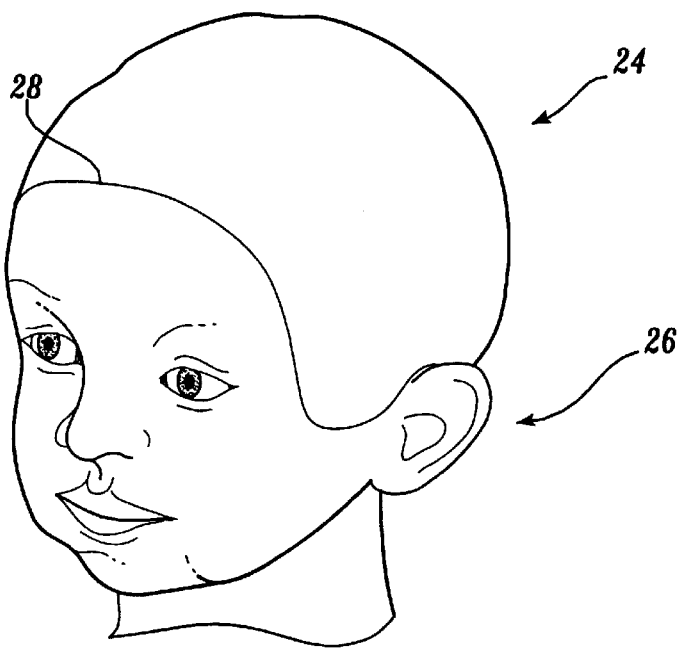

DEVICE FOR COOLING INFANT'S BRAIN

FIELD OF THE INVENTION

The present invention relates to a device for cooling the brain of an infant, particularly the brain of an infant that has suffered a hypoxic shock to the brain.

BACKGROUND OF THE INVENTION

Despite the advanced state of today's medical care, brain injury to newborn infants, e.g., after a difficult labor resulting in permanent neurological damage because the infant's brain did not receive sufficient oxygen-rich blood, occurs in an estimated 1 or 2 per 1000 births in the United States. Following the deprivation of the muchneeded oxygenated blood, neurons in the brain die over the course of minutes to days and are not capable of regeneration. In addition, glial cells which are essential for normal brain functioning can be lost.

There is scientific evidence that mild hypothermia of the affected infant's brain protects against neuronal damage in the case of hypoxic-ischemic insults to the brain. It has been reported that lowering the brain temperature to levels that are protective for neuronal damage facilitates improving the neurological and thus psycho-motor developmental outcome.

With this backdrop, several investigators have proposed particular devices for mild hypothermia of a newborn infant's brain. One such proposal is described and illustrated in the Dec. 16, 1997 edition of the *Wall Street Journal* and comprises a cooling cap wherein cooling water circulates through tubing that is coiled in a spiral configuration around the infant's head. The cooling water enters one end of the tubing adjacent the side of the infant's head and exits the tubing near the top of the infant's head.

Conventional tubing arranged in a spiral has a tendency to spring back and revert to its original shape. Therefore, external forces must be used to oppose the forces associated with the memory of the tubing over the entire surface of the infant's skull in order to maintain the tubing in contact with the head. While these forces may be effective to oppose the spring-back of the tubing, there is concern over the effect such forces have on the development on the newborn's fragile skull. Positioning the inlet for the cooling fluid near the side of the infant's head creates the risk that the infant may shift its head and thus pinch or otherwise impede flow into the tubing. Prior designs of cooling caps for an infant's head have not taken into account the change in temperature of the cooling fluid that occurs from the cooling fluid inlet to the cooling fluid outlet and the effect this has on cooling different portions of the brain. For example, in the cooling cap described above, the most extreme cooling occurs around the portion of the head just above the ears where the fluid enters the tubing and is the coldest, while less cooling would occur near the top of the head where the cooling fluid would be warmer.

Devices also exist for cooling the heads of adults, such as those undergoing chemotherapy treatment. It is reported that such treatment reduces the loss of hair as a result of the chemical treatment. An infant's skull is different in shape than an adult's skull, and is not fused and therefore very susceptible to external forces. The simple miniaturization of existing adult head cooling devices for use with infants is not appropriate due to the structural and shape differences between an adult skull and an infant skull.

In view of the foregoing, the need exists for an improved design for a device to cool an infant's brain so that effective utilization of the hypothermia treatment can be achieved.

SUMMARY OF THE INVENTION

The present invention relates to a device for cooling the brain of a newborn infant, for example, an infant that has suffered brain injury as a result of oxygen deprivation to the brain. The device for mild hypothermia of a newborn infant's brain protects the brain from or minimizes the effect of neuronal damage to the brain, thus improving the neurological and psychomotor developmental outcome.

A device formed in accordance with the present invention includes a cooling liner for placement on the infant's skull. The cooling liner comprises a fluid conduit that has an inlet for receiving a cooling fluid and an outlet for allowing the cooling fluid to leave the conduit. The fluid conduit is preferably serpentine in shape between the inlet and the outlet and configured so that the fluid conduit travels from the inlet adjacent a first hemisphere of the infant's brain in a general direction toward an opposite hemisphere of the infant's brain where the conduit reverses its direction and a serpentine portion of the conduit travels in a direction from the opposite hemisphere towards the first hemisphere where it terminates at the outlet. An outer cap may be provided over the cooling liner to help maintain the cooling liner in contact with the infant's skull.

In a specific embodiment, the cooling liner also includes fluid couplings connected to the inlet and the outlet that extend generally perpendicular from the inlet and outlet.

In a further embodiment of the present invention, the inlet and outlet are located near the top of the cooling liner which is adjacent to the top region of the infant's skull. This location is preferred because it is an area where the inlet and outlet can be positioned such that they do not interfere with the normal position of the infant's skull when prone or supine.

An optional inner liner comprising a material positioned to separate the infant's skull from the cooling liner may also be provided.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 1 is a perspective view of an infant's head with a preferred embodiment of a device formed in accordance with the present invention shown in an exploded view above the infant's skull;

DETAILED DESCRIPTION OF THE PREFERRED EMBODIMENT

A device for cooling an infant's brain formed in accordance with the present invention cools the infant's brain, particularly those portions that are most susceptible to neuronal damage as a result of an hypoxic-ischemic insult of the brain. Such portions of the brain include the parasagittal cortex, and other effected regions of the brain. While cooling portions of the brain described above, the device avoids cooling the infant's forehead and face to avoid "diver's reflex" which could result in the cessation of breathing by the infant. The device is designed to accommodate different skull shapes. In addition, the device is lightweight and fits the infant's skull in a manner that minimizes the external forces needed to hold the device in place and the forces exerted on the infant's fragile neck.

Referring to FIG. 1, the device includes a cooling liner 20, and an optional outer cap 22, and an optional inner liner 24. When inner liner 24 and outer cap 22 are employed, cooling liner 20 is sandwiched between inner liner 24 and outer cap 22. In those instances where inner liner 24 is not included, cooling liner 20 directly contacts the infant's skull, but not the infant's forehead, face or ears. As used herein, the phrase "infant's forehead" is considered to be that portion of the head that is directly above the face and which, if cooled too aggressively, initiates diver's reflex. In FIG. 1, the phrase "infants skull" is covered by inner liner 24 while the infant's forehead is not covered by inner liner 24.

Figure 9:
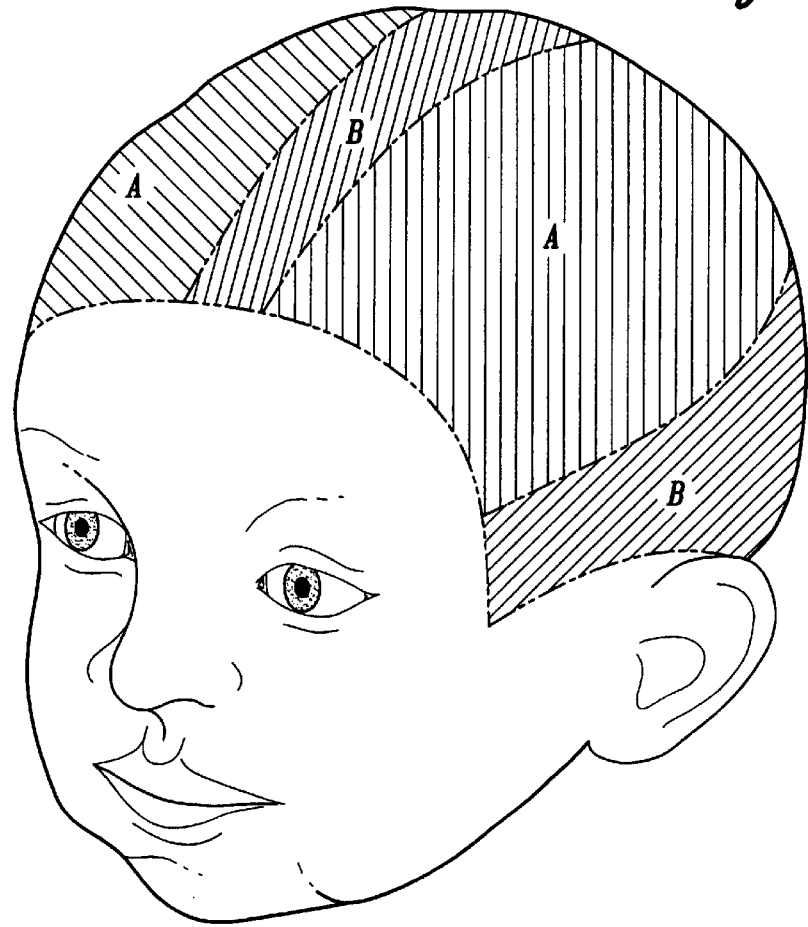
FIG. 9 is a perspective view of an infant's head illustrating portions of the infant's skull that are preferably cooled in accordance with the present invention.
Figure 10:
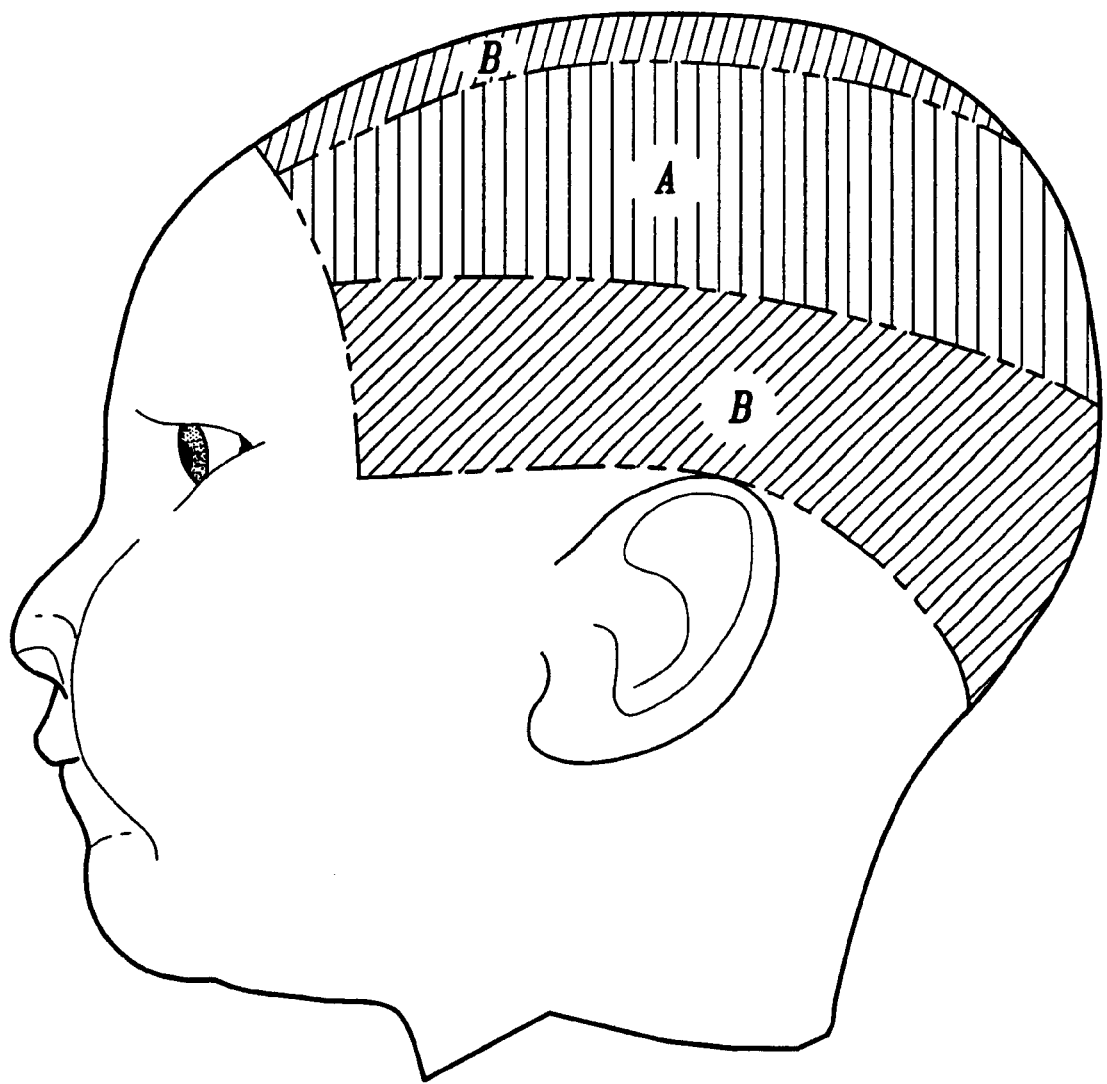
FIG. 10 is a left side elevation view of the infant's head of FIG. 9.
Figure 11:
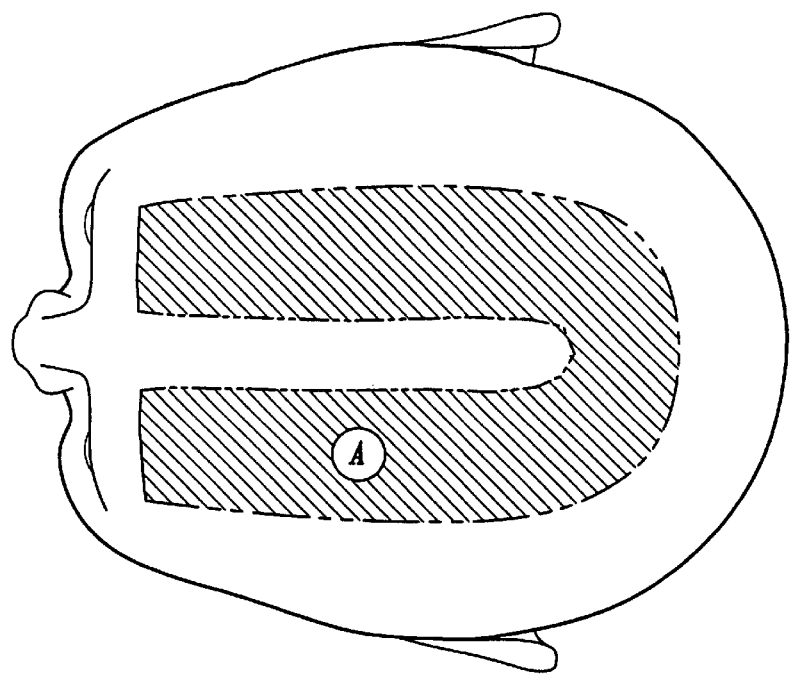
FIG. 11 is a top plan view of the infant's head of FIG. 9.

Referring to FIGS. 9, 10 and 11, the device for cooling an infant's brain formed in accordance with the present invention provides general cooling over the entire surface of the infant's skull with which it is contacted. As described below in more detail with respect to diver's reflex, certain portions of the infant's head should not be cooled by the device of the present invention; however, it is preferred that those segments designated by reference A be the focus of the cooling. Those portions identified by reference B can also be cooled in accordance with the present invention. Area A corresponds to that portion of the skull which protects the parasagittal cortex of the infant's brain along with other components of the infant's brain.

While the present invention is described below in the context of a particular embodiment, it should be understood that other configurations or materials can be employed without departing from the spirit and scope of the present invention.

Continuing to refer to FIG. 1, optional inner liner 24 is a member which serves as a contact barrier between inner surface 30 of cooling liner 20 and the infant's skull 26 to prevent the cooling liner from sticking to the infant's head. Preferably, inner liner 24 transports moisture, that may form on the infant's skull due to perspiration or from condensation on inner surface 30, away from the skull. The inner liner may achieve this transportation by promoting the evaporation of the moisture. In addition, inner liner 24 can include holes to facilitate ventilation. It is preferred that an inexpensive, disposable material be used to form inner liner 24. The material can be any medical grade material suitable for contact with the infant's skull, such as spun or woven polypropylene.

As illustrated in FIG. 1, inner liner 24 is placed over the infant's skull and may cover the infant's forehead or the infant's ears. It should be understood since inner liner 24 does not provide any cooling per se, the front edge 28 of inner liner 24 may extend down over the infant's forehead or over the infant's ears. Though not illustrated, in certain instances it may be desirable to provide openings in inner liner 24 so that portions of the skull, such as the anterior fontanel can be accessed. Inner liner 24 may be sized to fit over the skull or it may take the form of sheets of material that are simply laid upon the infant's skull. Inner liner 24 is preferably provided with fasteners so it can be attached to cooling liner 20.

Referring additionally to FIGS. 2–6, the device includes cooling liner 20 shaped to fit closely over the infant's skull and receive and distribute a cooling fluid around those portions of the skull that contain the portions of the brain that are to be cooled. Cooling liner 20 includes a fluid conduit 32 that begins at an inlet 34 and terminates at an outlet 36. In the illustrated embodiment of FIG. 1, inlet 34 and outlet 36 are positioned adjacent to each other along the top of the cooling liner 20 when positioned on the infant's skull. As used herein, the "top" of cooling liner 20 refers to that portion of cooling liner 20 which, when worn on an infant's head, would be above the perimeter of the infant's head along which the infant's head would normally rest when in a normal prone or supine position. Positioning inlet 34 and the outlet 36 at the top of the cooling liner 20 is preferred in order to avoid having the infant's head resting on the inlet and outlet and possibly constricting flow therethrough.

Figure 12:
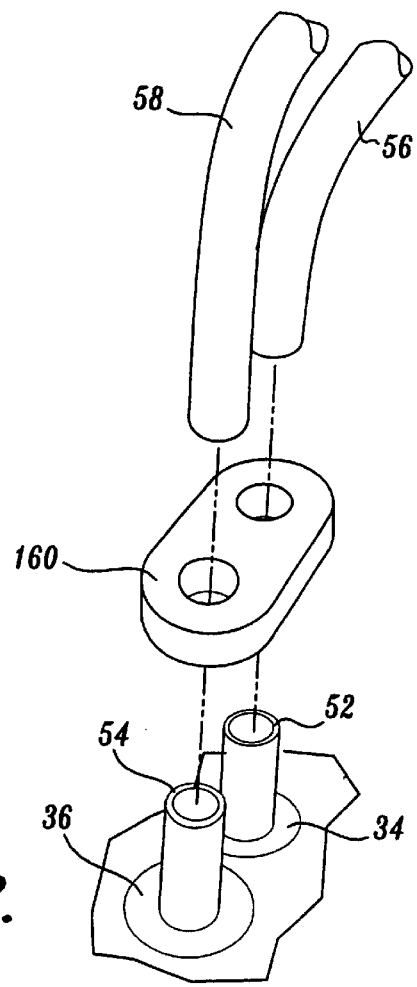
FIG. 12 is a detailed view of the inlet and outlet of the cooling liner of FIG. 1.

Referring additionally to FIG. 12, inlet 34 and outlet 36 are attached to inlet coupling 52 and outlet coupling 54 that comprise elongate annular members having one end attached to the respective inlet and outlet and the other end attached to either return tube 58 or supply tube 56. In order to protect the joint created between the inlet coupling 52 and inlet 34 and outlet coupling 54 and outlet 36, a block of reinforcement material is provided. Block 160 is a rectangular element which includes two bores passing therethrough for receiving a portion of inlet coupling 52 and outlet coupling 54. Block 160 serves to reinforce and help maintain the orientation of the inlet and outlet couplings relative to the surface of the cooling liner to which they are welded, thereby reducing the likelihood of occlusion of the water circulation. Block 160 helps to distribute forces that are applied to the inlet coupling 52 and outlet coupling 54 that could potentially cause these couplings to become disengaged from inlet 34 or outlet 36. Block 160 can be made from any lightweight resilient materials such as closed cell foam.

Figure 2:
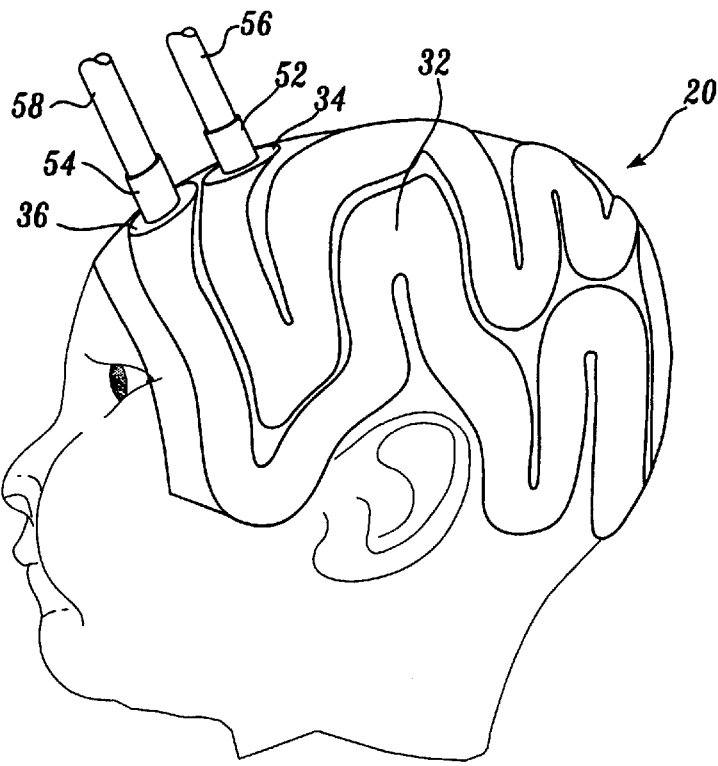
FIG. 2 is a left side elevation view of FIG. 1 with the outer cap removed and the cooling liner placed on the infant's skull.
Figure 3:
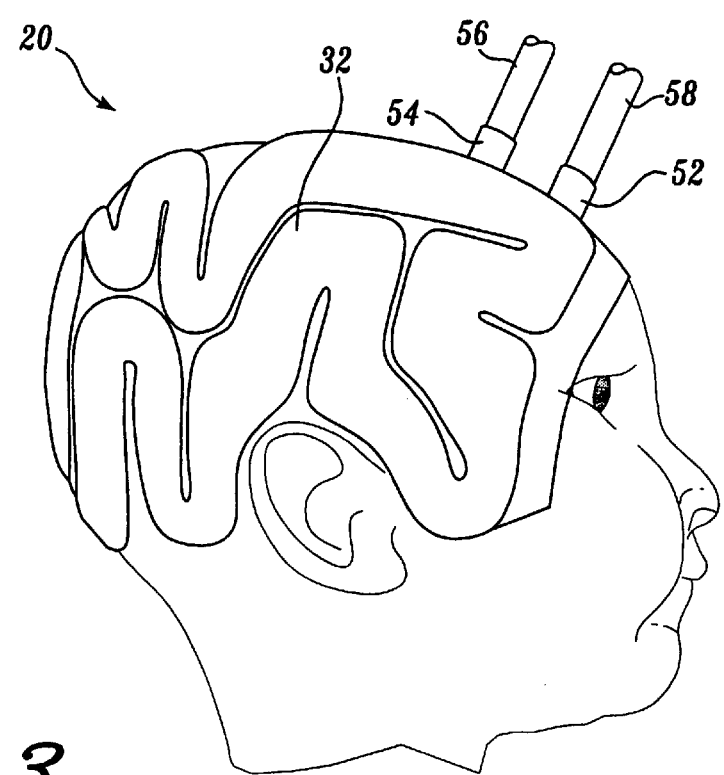
FIG. 3 is a right side elevation view of the device of FIG. 1 with the outer cap removed and the cooling liner placed on the infant's skull.
Figure 4:
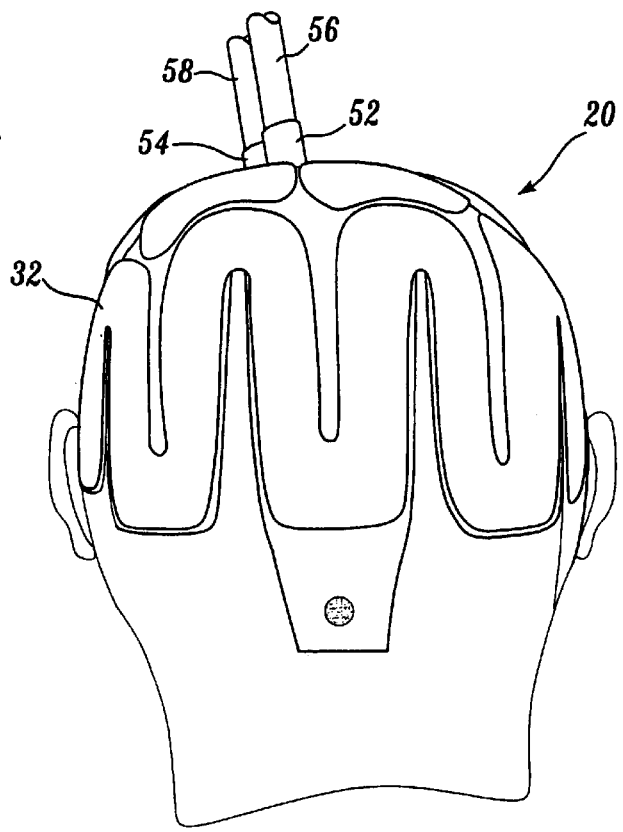
FIG. 4 is a rear elevation view of the device of FIG. 1 with the outer cap removed and the cooling liner placed on the infant's skull.
Figure 5:
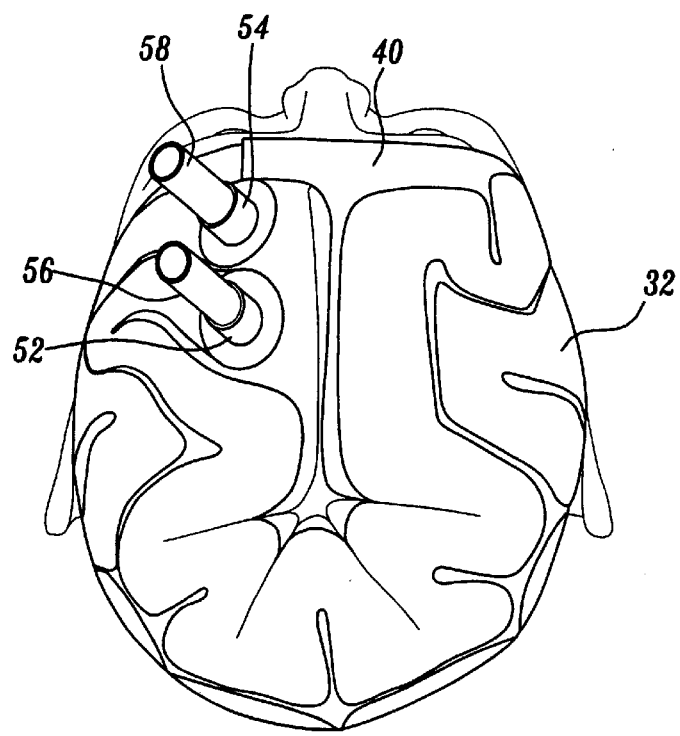
FIG. 5 is a top plan view of the device of FIG. 1 with the outer cap removed and the cooling liner placed on the infant's skull.
Figure 6:
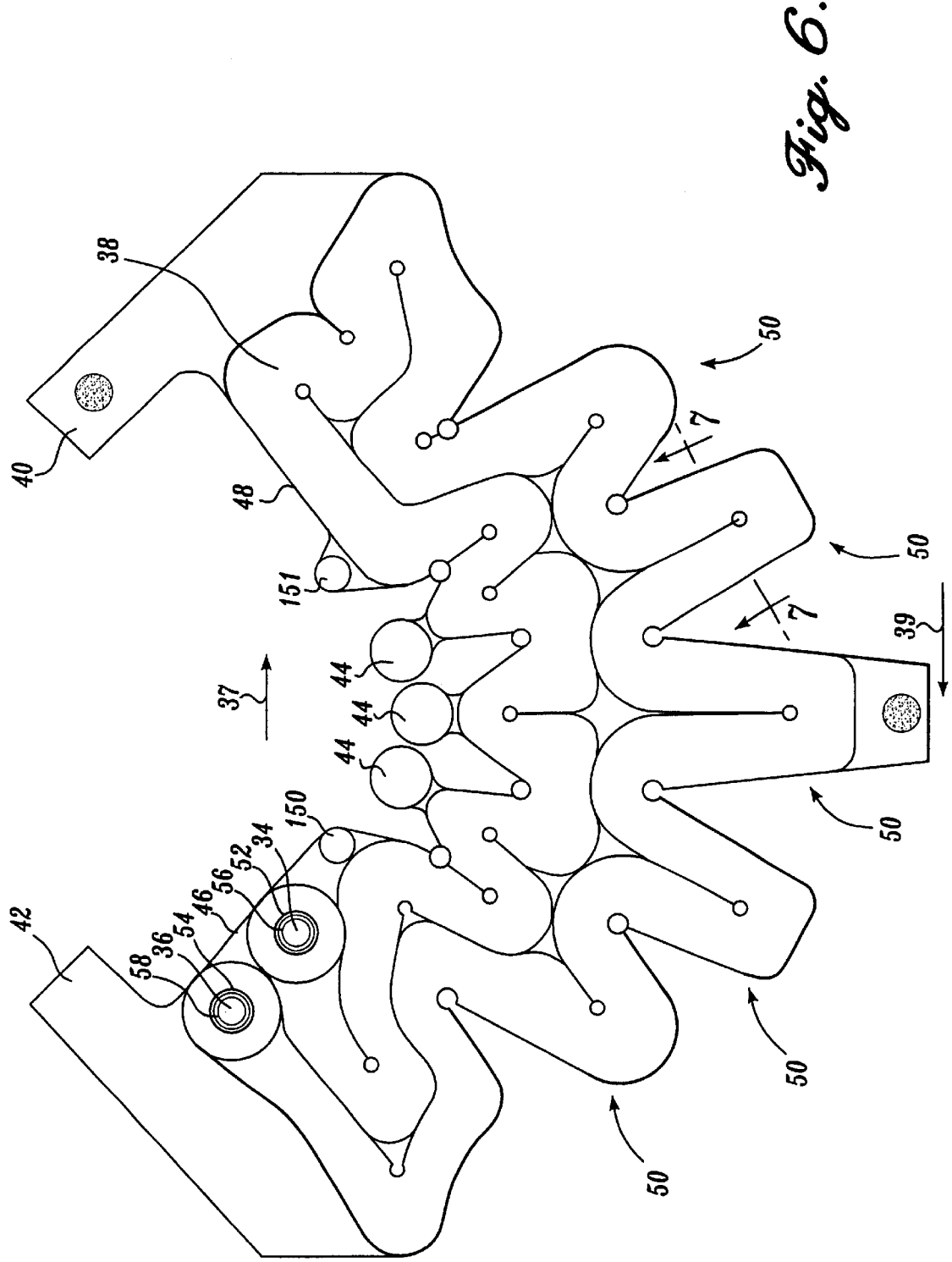
FIG. 6 is a top plan view of the cooling liner when removed from the infant's skull and laid flat.

As best illustrated in FIG. 1 and FIG. 6, fluid conduit 32 between inlet 34 and outlet 36 travels a serpentine path from the left hemisphere of the skull in the general direction of arrow 37 towards the right hemisphere generally over those portions "A" of the skull illustrated in FIGS. 9 and 10. At a location generally indicated by 38, fluid conduit 32 begins its return to the outlet 36 along a serpentine path that travels in the general direction of arrow 39 from the right hemisphere towards the left hemisphere over region "B". It should be understood that while a particular shape for the path of fluid conduit 32 is illustrated and preferred, other shapes may also provide the advantages of the present invention as described below in more detail.

The specific layout of cooling liner 20 provides cooling to those portions of the brain where cooling appears to provide the most benefit in mitigating neuronal damage, e.g., area A, while at the same time avoiding the infant's forehead and ears. A cooling liner is preferably formed as a flat member because of the ease of manufacturing and the relatively low cost. Referring to FIG. 6, cooling liner 20 comprises a first portion of fluid conduit 32 extending from inlet 34 to approximately return point 38 and a second portion extending from return point 38 to outlet 36. The path of the second portion takes the fluid conduit through a number of radially extending fingers 50. In the embodiment of FIG. 6, five fingers are illustrated, although a larger or smaller number of fingers would also be suitable. Extending from the first portion of fluid conduit 32 in a direction opposite to the direction that radial fingers 50 extend, are three circular tabs 44. Fluid conduit also includes a rectangular tab 42 which extends outward from the fluid conduit 32 adjacent outlet 36. On the opposite side of cooling liner 20, a rectangular closure flap 40 extends outward from the fluid conduit approximately adjacent return point 38. Overlapping flap 40 and tab 42 may carry some type of fastener, such as a hook and loop fastener or snaps. Circular tabs 44 may also be provided with fasteners. In order to shape cooling liner 20 to the skull of an infant, circular tabs 44 are caused to be superimposed on each other and tab 42 is overlaid by closure flap 40. Additional securing tabs can also be provided in order to customize the fit of cooling liner 22 to the infant's skull.

Cooling liner 20 defines a left mating edge 46 that extends approximately between circular tabs 44 and tab 42. Located between circular tabs 44 and closure flap 40 is a right mating edge 48. When closure flap 40 and tab 42 are superimposed on each other, left mating edge 46 and right mating edge 48 are brought together so that they abut approximately along the center line of cooling liner 20. When positioned on the infants skull, the abutting left edge 46 and right edge 48 are preferably positioned along the center line of the infant's skull. By so positioning these mating edges, when closure flap 40 and tab 42 are disengaged, and cooling liner is opened up along these edges, access to the anterior fontanel is possible. In addition to providing access to the anterior fontanel, the ability to overlap closure flap 40 and tab 42 allows for adjustment of the size of the cooling liner so that different shaped skulls can be fitted using the same size cooling liner 20. Additional fastening tabs 150 and 151 can be provided along edges 46 and 48.

Cooling liner 20 may also include apertures to promote ventilation above and below cooling line 20.

As noted above, fluid conduit 32 follows a serpentine path from inlet 34 to outlet 36. As used herein, "serpentine" refers to a meandering pathway that is not spiral in shape. In a spiral configuration, the fluid repeatedly, i.e., more than once, passes over the left hemisphere to the right hemisphere of the infant's brain and from the right hemisphere to the left hemisphere. In contrast, the serpentine path of a fluid conduit formed in accordance with the present invention transports the fluid in the general direction of arrow 37 over the left hemisphere and then to the right hemisphere once and then returns the fluid in the general direction of arrow 39 over the right hemisphere and then the left hemisphere once. The particular shape of the serpentine path is preferably selected to minimize the number of compound curves that are present in order to reduce the risk of constriction to flow. Minimizing the number of compound curves should be balanced against selecting a shape for the fluid conduit that provides cooling to the desired portion of the infant's brain.

For example, when it is desired to cool the parasagittal cortex, the path of fluid conduit 32 should be selected so that the cooling fluid when it is the coldest is caused to flow over that portion of the skull which protects the parasagittal cortex, e.g., area "A". As the cooling fluid warms, the fluid conduit can carry the cooling fluid over those portions of the skull protecting those portions of the brain where cooling is less critical, e.g., area "B". In certain instances, it may be desirable to provide maximum cooling to portions of the infant's brain other than a parasagittal cortex. In those instances, a serpentine path different from that illustrated in FIG. 1 may be preferred.

Fingers 50 permit cooling liner 20 to fit infants with different shaped skulls. Fingers 50 also reduce the strain, e.g., spring back, within cooling liner when it is transformed from its flat configuration to the shape of the infant's skull. In addition, the material of the cooling liner tends to act like a hinge along the welded seams. By reducing internal strain, there is less tendency for the cooling liner to spring back to its original flat configuration. Minimizing the spring back force is desirable because it reduces the amount of external force needed to maintain the cooling liner in contact with the infant's skull.

The serpentine path of fluid conduit 32 comprises a plurality of bends and curves separating relatively straight segments. In the illustrated embodiment, the cross-sectional area of the bends and curves is preferably selected to be greater than the cross-sectional area of the straight segments. By selecting the cross-sectional area of the bends and curves to be greater than the cross-sectional area of the straight segments of the fluid conduit, any loss of flow that would normally occur (if the cross-sectional area was maintained) along these curves due to a change in direction of the flow is reduced or mitigated.

Figure 7:
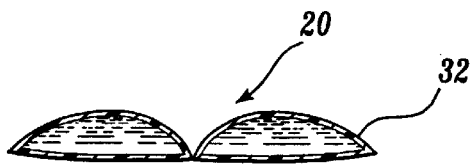
FIG. 7 is a cross section of the cooling liner taken along line 7—7 in FIG. 6.

The particular cross-sectional shape of fluid conduit 32 is not critical although it is preferred that conduit 32 have maximum contact with those portions of the skull overlying those portions of the brain to be cooled. In order to maximize the contact, referring to FIG. 7, it is preferred that the conduit be relatively flat or oval in cross section as opposed to round, although round could be used. The cross-sectional area of the fluid conduit must take into consideration several factors, including the desired flow rate and the pressure needed to maintain such flow rate given the size of the conduit. Generally, high flow rates are preferred so that the change in temperature of the cooling fluid from the inlet to the outlet is minimal. On the other hand, such high flow rates may require greater pressures for a given cross-sectional area. Increasing pressure encourages the fluid conduit to spring back to its flat configuration which is described above is undesirable. The design described above seeks to provide a high flow rate and a low pressure.

By way of example, the fluid conduit has a cross-sectional area of about 0.05 in$^2$–0.10 in$^2$. For a fluid conduit to have a cross-section within the above range, internal pressures less than 5.0 psi and flow rates ranging from 1.0 liter/minute to 0.5 liter/minute provide acceptable combinations of pressure and flow rate. The pressure used should be selected to avoid occlusion of the fluid flow as a result of forces created by the weight of the infant's head and the weight of the device. As discussed above, the pressure should not be so high that it creates an excess amount of "spring back" of the cooling liner.

In the illustrated embodiment, a single fluid conduit 32 is illustrated. While multiple conduits could be used, and may be advantageous when particular regions of the brain require specific cooling, generally a single conduit is preferred because it provides relatively simple monitoring to determine if a blockage or constriction to flow has occurred.

In order to avoid diver's reflex, wherein the infant ceases breathing because the forehead or face has been excessively cooled, cooling liner 20 is shaped so that when properly seated on the infant's skull cooling fluid does not pass over the infant's forehead.

Suitable methods of manufacturing cooling liner 20 include heat welding or radio frequency (RF) welding two sheets of weldable material together.

The materials used to form cooling liner 20 can be any medical grade material suitable for skin contact. For example, polyurethane, polyvinyl chloride or polyethylene can be used. Other types of plastics which are lightweight and RF- or heat-weldable can be employed. The thickness of the material used to form cooling liner 20 is chosen taking into consideration, among other things, the heat transfer properties, strength, flexibility, and processability.

In addition to the heat-welding or RF-welding of thin films together to form the channels, other techniques may be employed. For example, the outer layer of cooling liner 20 could be vacuum formed so that the channels are set and therefore do not need to be "inflated" by the cooling fluid. Alternatively, a thicker or thinner material could be used in the top or bottom layer in order to tailor the surface of cooling liner 20 that expands the most. For example, the upper surface could be thinner than the lower surface. In such a case, when inflated, the upper surface would tend to inflate more than the lower surface because of the rigidity of the lower surface. By maintaining the lower surface flat, better contact occurs between this surface of the cooling liner, which improves the heat transfer rate. It is not required that the films used to form cooling liner be identical. For instance, the top film could be an elastic material and the bottom film nonelastic, or vice versa.

Continuing to refer to FIGS. 1–6, cooling liner 20 includes inlet coupling 52 and outlet coupling 54 which extend from inlet 34 and outlet 36, respectively. Inlet coupling 52 and outlet coupling 54 are tubular members which extend from cooling liner 20 and are welded or otherwise adhered to cooling liner 20 to provide a semi-rigid attachment for supply tube 56 and return tube 58. Supply tube 56 delivers cooling fluid from a cooling fluid source (not illustrated) and return tube 58 delivers cooling fluid to the source. Inlet coupling 52 and outlet coupling 54 are provided so that a secure connection can be made between supply and return tubes and the inlet and outlet to fluid conduit 32. In the illustrated embodiment, inlet coupling 52 and outlet coupling 54 extend from cooling liner 20 in a direction that is substantially perpendicular from inlet 34 and outlet 36. Preferably, these couplings extend in a direction that is substantially parallel to the longitudinal axis of the infant. This positioning is preferred so that the infant's head does not interfere with the free flow of cooling fluid into and out of cooling liner 20. As used herein, the longitudinal axis of the infant refers to a direction that is generally along the length of the baby, parallel to its spine. It is within the scope of the present invention that the inlet coupling and the outlet coupling extend in directions other than parallel to the longitudinal axis of the infant; however, when such is the case, care must be taken that movement of the infant's head will not result in a constriction of cooling fluid flow into or out of cooling liner 20.

In the embodiment illustrated in FIGS. 1–6, inlet 34 and outlet 36 are positioned adjacent to each other. This positioning is preferred because it allows the cooling fluid at its coldest temperature to enter at a point adjacent to where the cooling fluid at its warmest exits fluid conduit 32. The path of fluid conduit 32 preferably takes the coldest cooling fluid and carries it past a portion of the fluid conduit carrying the warmest cooling fluid. As the coldest cooling fluid begins to warm, the path of fluid conduit 32 takes it past portions of the fluid conduit carrying cooling fluid that is colder than the warmest fluid. By directing the flow of cooling fluid in this manner, the average of the temperature of the cooling fluid in adjacent portions of fluid conduit 32 is maintained in a relatively narrow band. This helps to provide an even cooling treatment to the infant's brain, particularly over area "A", i.e., the cooling effect to (or heat transfer from) the left hemisphere and the right hemisphere is preferably the same.

Figure 8:
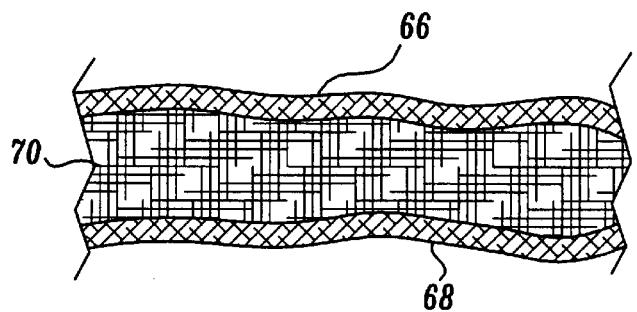
FIG. 8 is a cross section of the material forming the outer cap in FIG. 1.

A cooling device formed in accordance with the present invention also preferably includes an outer cap designed to help retain cooling liner 20 in position on the infant's skull. Referring to FIGS. 1 and 8, an outer cap 22 shaped to fit over cooling liner and over the infant's skull is provided to distribute the force of the infant's head and provide a thermal barrier. Outer cap 22 is generally shaped to be congruent with cooling liner 20. The front of outer cap 22 includes an access slit 60 which can be closed by sealing overlapping flap 62 over access slit 60. The portion of outer cap 22 overlapped by flap 62 can carry a hook or loop fastener with the flap carrying the opposite fastener. Alternatively, hooks or snaps can be provided to close the opening. Access slit 60 is positioned on outer cap 22 to permit access to the midline seam of cooling liner 20 thus allowing medical personnel access to the anterior fontanel. In addition to providing access to the anterior fontanel, closure flap also provides a means for adjusting the size of outer cap 22 so that skulls of different sizes can be fitted using the same size outer cap. Additional means can be provided to retain outer cap 22 on the infant's head, such as a chin strap of adjustable length.

Outer cap 22 is also be designed to avoid or reduce the collapse or constriction of fluid conduit 32 as a result of the weight of the infant's head lying on a mattress, or other supporting surface. Since an infant is unable to support the weight of its own head, the normal position for the infant to be treated is prone or supine with its head resting on a mattress or pillow. In order to avoid constriction or collapse of fluid conduit 32 at those locations where the infant's head is resting on the mattress, provisions must be made to reduce the force imparted on the fluid conduit. One way to achieve this result is to increase the surface area over which the force is exerted and provide padding in the outer cap. The material chosen to provide padding in the outer cap can also provide a thermal insulative layer.

Outer cap 22 also includes apertures 64 permitting supply tube 56 and return tube 58 to pass through outer cap 22. In addition, the outer cap preferably includes fasteners for attaching cooling liner 20 to elastic layer 68.

The size of outer cap is selected so that it provides enough restriction to oppose any spring-back created when cooling fluid is distributed through cooling liner 20. The force exerted by outer cap 22 should be sufficient to oppose this springback but not so great as to cause injury to the infant's skull as a result of the restraining pressure. Though not illustrated, additional restraining structures such as straps or belts can be employed to further retain outer cap 22 on the infant's head. Any such restraining devices should avoid unnecessary strain on the neck, such as twisting motion as the cooling liner expands.

Referring specifically to FIG. 8, in one embodiment, the outer cap includes an outer infrared reflective layer 66 and an opposing elastic layer 68 spaced from the infrared reflective layer. Sandwiched between infrared reflective layer 66 and elastic layer 68 is insulative layer 70. Infrared reflective layer is chosen from materials that will reflect infrared radiation directed toward the infant to heat other body segments such as the torso. Examples of suitable infrared reflective materials include metallized polyester or cloth. Elastic layer 68 can be selected from any suitable medically acceptable material such as polyurethane fibers commercially available, under the trade names Lycra™ or Spandex™. The insulative layer is preferably a high loft material used in an amount/thickness sufficient to provide enough cushioning to prevent the weight of the infant's head from constricting the underlying fluid conduit of the cooling liner. Examples of suitable insulative material include spun polyester (e.g., Holo-Fil™) or closed cell foam. While the outer cap described above is effective to reduce the amount of constriction on fluid conduit 32, other means may also be employed such as providing foam pad inserts to act as spacers for supporting the infant's head such that it does not constrict fluid conduit 32. As an alternative to spacers, splines or ridges could be provided over the cooling liner 20 in order to provide support for the infant's head. The use of a cushion or pillow may also help to avoid constriction of fluid conduit 32 by the weight of the infant's head.

Though not illustrated, outer cap 22 can be provided with ventilation holes or channels in order to reduce condensation within the cap.

As an alternative to inner liner 24, or an addition thereto, conductive creams or other heat transfer media could be provided between the infant's scalp and cooling liner 20.

All of the materials and structure chosen for the device of the present invention should be as lightweight as possible in order to avoid any unnecessary pressure on the skull and forces on the infant's neck.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A device for cooling the brain of an infant whose brain has suffered a hypoxic shock, the device comprising:

a cooling liner for placement on the infant's skull, the cooling liner having a top and comprising only one fluid conduit for receiving a cooling fluid, the fluid conduit beginning at an inlet located at the top and terminating at an outlet located at the top, being serpentine in shape between the inlet and the outlet and configured so that the fluid conduit travels from the inlet adjacent a first hemisphere of the infant's brain in a general direction toward an opposite hemisphere of the infant's brain where the conduit reverses its direction and a serpentine portion of the conduit travels in a direction from the opposite hemisphere to the first hemisphere where it terminates at the outlet, the cooling liner including fluid couplings connected to the inlet and outlet that extend generally perpendicular from the inlet and outlet and further including, a plurality of bends, the cross sectional area of the fluid conduit along the bends being greater than the cross sectional area of the fluid conduit entering the bends.

2. The device of claim 1, further comprising:

an outer cap shaped to encompass the cooling liner and maintain a portion of the cooling liner in contact with the infant's skull.

3. The device of claim 1, wherein the inlet is adjacent to the outlet.

4. The device of claim 1, wherein the fluid conduit is shaped to cool the top, sides and rear of the infant's brain without directly cooling the forehead.

5. The device of claim 1, further comprising an inner liner to be interposed between the infant's skull and the cooling liner.

6. The device of claim 1, wherein the cooling liner further comprises a plurality of fingers occupied by the fluid conduit that extend from the top of the cooling liner downward to cool the rear of the infant's skull.

7. The device of claim 6, comprising at least three fingers.

8. The device of claim 1 wherein the fluid conduit near the inlet lie adjacent to the fluid conduit near the outlet.

9. The device of claim 1, wherein the cooling liner comprises at least one sheet of a heat weldable material.

* * * * *

UNITED STATES PATENT AND TRADEMARK OFFICE
CERTIFICATE OF CORRECTION

PATENT NO. : 6,312,453 B1
DATED : November 6, 2001
INVENTOR(S) : J.P. Stefanile et al.

It is certified that error appears in the above-identified patent and that said Letters Patent is hereby corrected as shown below:

Title page,
Item [56], References Cited, OTHER PUBLICATIONS,

"*Care med.*;" should read -- *Care Med.*; --
"Resuscitationn" should read -- Resuscitation --

Column 10,
Line 43, "lie" should read -- lies --

Signed and Sealed this

Twenty-third Day of April, 2002

Attest:

JAMES E. ROGAN
Attesting Officer    Director of the United States Patent and Trademark Office